US00PP16555P2

(12) United States Plant Patent
Leue

(10) Patent No.: US PP16,555 P2
(45) Date of Patent: May 16, 2006

(54) *ANGELONIA* PLANT NAMED 'BALANGBAWI'

(50) Latin Name: *Angelonia angustifolia*
Varietal Denomination: Balangbawi

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 59 days.

(21) Appl. No.: 11/022,708

(22) Filed: Dec. 27, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Angelonia* plant named 'Balangbawi' characterized by its white-colored flowers, dark green-colored foliage, and trailing, well-branched growth habit.

1 Drawing Sheet

Latin name of genus and species of plant claimed: *Angelonia angustifolia.*
Variety denomination: 'Balangbawi'.

BACKGROUND OF THE INVENTION

The present invention relates to a new and distinct cultivar of *Angelonia* plant botanically known as *Angelonia angustifolia* and hereinafter referred to by the cultivar name 'Balangbawi'.

The new cultivar was developed by the inventor in a controlled breeding program during June 2001 at Elburn, Ill. The objective of the breeding program was the development of *Angelonia* cultivars with freely branching, trailing, and vigorous growth habits, unique flower colors, and continuous flowering.

The female (seed) parent of the new cultivar was the proprietary *Angelonia angustifolia* breeding selection designated 107-19, not patented, characterized by its white-colored flowers and mounded growth habit. The male (pollen) parent of the new cultivar was the proprietary *Angelonia angustifolia* breeding selection designated 107-20, not patented, characterized by its violet-colored flowers and semi-spreading growth habit. The new cultivar was discovered and selected by the inventor as a single flowering plant within the progeny of the above stated cross-pollination during April 2002 in a controlled environment at Elburn, Ill.

Asexual reproduction of the new cultivar by terminal stem cuttings since April 2002 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangbawi' as a new and distinct cultivar of *Angelonia* plant.

1. White-colored flowers.
2. Dark green-colored foliage.
3. Trailing, well-branched growth habit.

Plants of the new cultivar differ from plants of the female parent primarily in growth habit and from plants of the male parent primarily in growth habit and flower color.

Of the *Angelonia* cultivars known to the inventor, the most similar to 'Balangbawi' is the *Angelonia* cultivar Balangloud (U.S. Plant Pat. No. 15,306). However, in side-by-side comparisons, carried out at West Chicago, Ill., plants of the new cultivar differ from plants of 'Balangloud' primarily in growth habit.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangbawi'. The plants were grown in 25 cm pots for 16 weeks in a greenhouse at West Chicago, Ill.

DETAILED BOTANICAL DESCRIPTION

Figure 1:
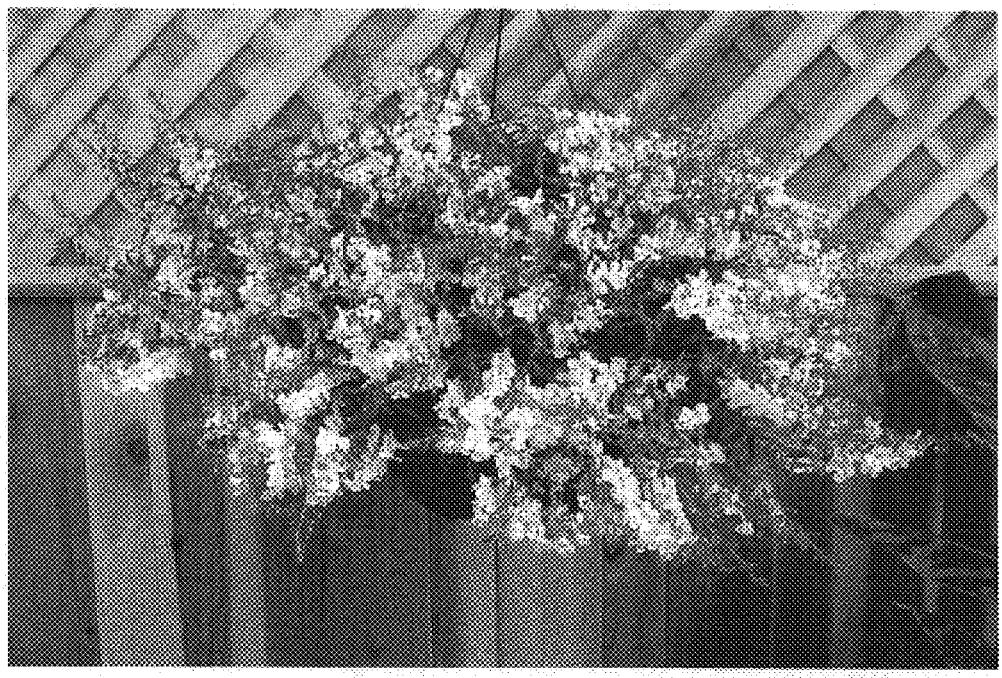
FIG. 1 illustrates a side view of the overall growth and flowering habit of 'Balangbawi' with three plants per pot.
Figure 2:
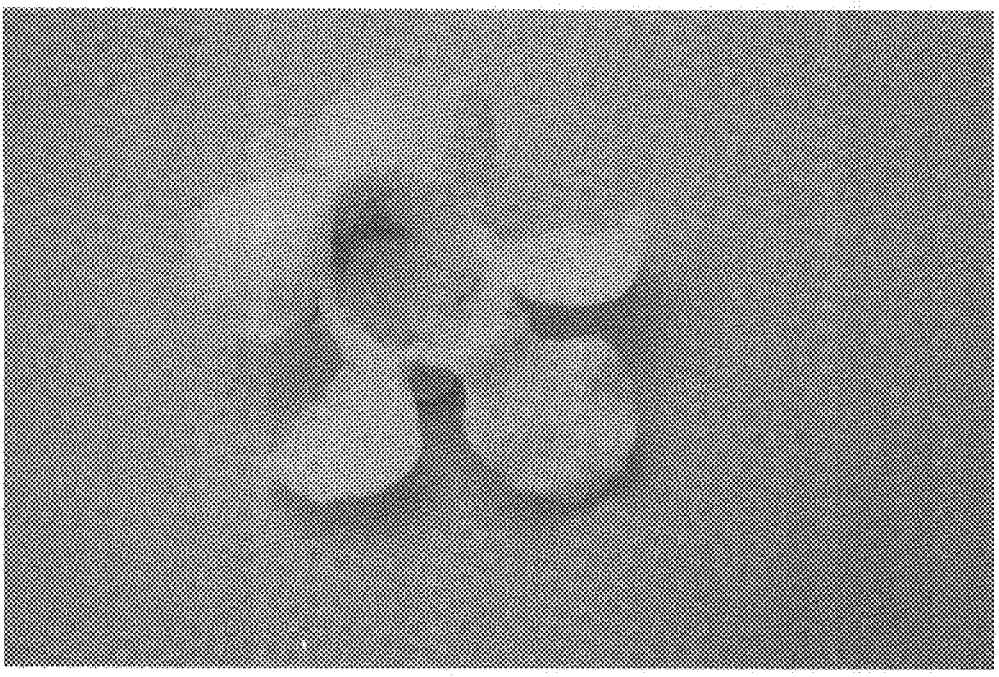
FIG. 2 illustrates a close-up view of an individual flower of 'Balangbawi'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 21, 2004. The readings were taken between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 14 weeks while utilizing a soilless growth medium. Greenhouse temperatures were maintained at approximately 75°–85° F. (24°–29° C.) during the day and approximately 62°–70° F. (17°–21° C.) during the night. Greenhouse light levels were maintained at approximately 6,000 to 10,000 footcandles during the day.

Botanical classification: *Angelonia angustifolia,* cultivar Balangbawi.

Parentage:

*Male (pollen) parent.*—Proprietary *Angelonia angustifolia* breeding selection 107-20, not patented.

*Female (seed) parent.*—Proprietary *Angelonia angustifolia* breeding selection designated 107-19, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous with good branching.

*Form.*—Trailing.

*Size.*—Height (from soil level to top of plant plane): Approximately 12.7 cm. Length (from soil level to tip of longest hanging branch: Approximately 17 cm. Diameter (area of spread): Approximately 59 cm in diameter.

*Main branch.*—Quantity per plant: Approximately 4. Shape: Square in cross section. Strength: Moderate. Length from soil level to base of raceme: Approximately 30.9 cm. Diameter: Approximately 2.6 mm. Texture: Glabrous. Color: 144C. Internode length at middle of branch: Approximately 1.6 cm.

*Foliage.*—Quantity of leaves per branch: Approximately 18. Type: Simple. Fragrance: None. Arrangement: Opposite. Orientation to stem: At right angle to obtuse. Shape: Lanceolate. Margin: Dentate. Apex: Acute. Base: Sessile. Length of leaf taken from middle of branch: Approximately 6.3 cm. Leaf width: Approximately 1.3 cm. Texture of upper and lower surfaces: Glabrous. Venation pattern: Pinnate. Color of upper surface of young and mature foliage: 139A with venation of 144C. Color of lower surface of young and mature foliage: 146A with venation of 144C.

Flowering description:

*Flowering habit.*—'Balangbawi' is freely flowering under outdoor growing conditions with substantially continuous blooming from spring through autumn and year round in greenhouse environment.

*Lastingness of individual bloom.*—Approximately 7 to 10 days.

*Inflorescence type/description.*—Terminal racemes. Length: 6.9 cm. Width: 4.8 cm. Number per plant: Approximately 6 open racemes per plant. Number of fully open flowers per raceme at any one time: Approximately 14.

Flower description:

*Type/fragrance.*—Solitary, bi-labiate, persistent. Flowers have a slightly sweet fragrance.

*Flower size/aspect.*—Length: Approximately 2.2 cm. Width: Approximately 1.6 cm. Depth: Approximately 7.4 mm. Aspect: Facing outward.

*Petals.*—Quantity: Five per flower, fused at base forming a throat, an upper lip having two petals and a lower lip having three petals.

*Upper lip.*—Petal apex: Obtuse. Petal margin: Entire. Length of petals: Approximately 6 mm. Width of petals: Approximately 7 mm. Color of upper surface: Closest to 155B. Color of lower surface: 155B. Petal texture: Glabrous at margin, densely glandular at base. Gland color: Colorless, translucent.

*Lower lip.*—Petal apex: Obtuse. Petal margin: Entire. Length of petals: Approximately 8 mm. Width of petals: Approximately 8 mm. Color of upper surface: Closest to 155B. Color of lower surface: 155B. Texture: Glabrous at margin, densely glandular at base. Gland color: Colorless, translucent.

*Throat.*—Length: Approximately 7 mm. Width: Approximately 5 mm. Depth: Approximately 3.4 mm. Texture of inner and outer surfaces: Glabrous. Color of inner surface: 155B with area of 144C at base of stamens. Color of outer surface: 155B with 144C around pedicel attachment point.

*Pedicel.*—Strength: Good. Length: Approximately 1.3 cm. Diameter: Approximately 0.5 mm. Angle to stem: Acute. Texture: Glabrous. Color: 144C.

*Bud.*—Shape: Spherical. Length: Approximately 6.3 mm. Diameter: Approximately 6 mm. Color: 150D.

*Calyx.*—Shape: Five pointed star. Length: Approximately 4.0 mm. Width: Approximately 5.0 mm. Sepal shape: Lanceolate. Sepal margin: Entire. Sepal apex: Acuminate. Sepal length: Approximately 4 mm. Sepal width: Approximately 1.8 mm. Sepal texture: Upper and lower surface: Puberulent. Sepal color: Both surfaces: 144B.

*Reproductive organs.*—Androecium: Stamen quantity: Four per flower. Stamen length: Approximately 3.3 mm. Filament color: N155D. Anther length: Approximately 1.7 mm. Anther color: 155D. Amount of pollen: Moderate. Pollen color: 11D. Gynoecium: Pistil quantity: One per flower. Pistil length: Approximately 4.7 mm. Stigma length: Approximately 0.4 mm. Stigma color: Colorless and translucent. Style length: Approximately 3 mm. Style color: N155D. Ovary diameter: Approximately 1.1 mm. Ovary color: 150C.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangbawi' substantially, as herein shown and described.

* * * * *